US009375472B2

(12) United States Patent
Pitard

(10) Patent No.: US 9,375,472 B2
(45) Date of Patent: Jun. 28, 2016

(54) USE OF A GLYCOSYLATED-MODIFIED TETRAFUNCTIONAL NON-IONIC AMPHIPHILIC BLOCK COPOLYMER AS IMMUNE ADJUVANT

(71) Applicants: INSTITUT NATIONAL DE LA SANTE ET DE LA RECHERCHE MEDICALE, Paris (FR); CENTRE NATIONAL DE LA RECHERCHE SCIENTIFIQUE, Paris (FR); UNIVERSITE DE NANTES, Nantes (FR)

(72) Inventor: Bruno Pitard, Nantes (FR)

(73) Assignees: Institut National de la Sante et de la Recherche Medicale (INSERM), Paris (FR); CENTRE NATIONAL DE LA RECHERCHE SCIENTIFIQUE (CNRS), Paris (FR); UNIVERSITE DE NANTES, Nantes (FR)

( * ) Notice: Subject to any disclaimer, the term of this patent is extended or adjusted under 35 U.S.C. 154(b) by 9 days.

(21) Appl. No.: 14/382,117

(22) PCT Filed: Mar. 1, 2013

(86) PCT No.: PCT/IB2013/051659
§ 371 (c)(1),
(2) Date: Aug. 29, 2014

(87) PCT Pub. No.: WO2013/128423
PCT Pub. Date: Sep. 6, 2013

(65) Prior Publication Data
US 2015/0050297 A1    Feb. 19, 2015

(30) Foreign Application Priority Data
Mar. 2, 2012  (EP) .................. 12305256

(51) Int. Cl.
*A61K 39/00* (2006.01)
*A61K 39/39* (2006.01)
*A61K 47/48* (2006.01)

(52) U.S. Cl.
CPC ............. *A61K 39/39* (2013.01); *A61K 39/0005* (2013.01); *A61K 47/48092* (2013.01); *A61K 47/48215* (2013.01); *A61K 2039/55511* (2013.01); *A61K 2039/575* (2013.01)

(58) Field of Classification Search
CPC .............. A61K 2039/55511; A61K 2039/575; A61K 39/0005; A61K 39/39; A61K 47/48092
USPC ........................... 424/184.1, 278.1; 536/17.9
See application file for complete search history.

(56) References Cited

U.S. PATENT DOCUMENTS

| 5,376,369 A | 12/1994 | Allison et al. |
| 5,977,081 A | 11/1999 | Marciani |
| 2005/0192248 A1 | 9/2005 | Tsuji et al. |

FOREIGN PATENT DOCUMENTS

WO    2009/093007 A2    7/2009

OTHER PUBLICATIONS

McIlroy et al. (Molecular Therapy, vol. 17, No. 8, Published Aug. 2009, pp. 1473-1481).*
Petrovsky et al. (Immunology and Cell Biology, Published 2004, pp. 488-496).*
Jiang et al., "Monophosphoryl lipid A analogues with varying 3-0-substitution: synthesis and potent adjuvant activity", Carbohydrate Research, Feb. 27, 2007, pp. 784-796, vol. 342, No. 6, Pergamon, GB.
Adel-Patient et al., "Block Copolymers Have Differing Adjuvant Effects on the Primary Immune Response Elicited by Genetic Immunization and on Further Induced Allergy", Clinical and Vaccine Immunology, Nov. 18, 2009, pp. 36-42, vol. 17, No. 1.
Newman et al., "Development of adjuvant-active nonionic block copolymers", Advanced Drug Delivery Reviews, Jul. 1, 1998, pp. 199-223, vol. 32, No. 3, Elsevier BV, Amsterdam, NL.
Gavrilov et al, "Effects of glycosylation on antigenicity and immunogenicity of classical swine fever virus envelope proteins", Virology 420 (2011) 135-145.

* cited by examiner

*Primary Examiner* — Alma Pipic
(74) *Attorney, Agent, or Firm* — Whitham, Curtis & Cook, P.C.

(57) ABSTRACT

The present invention relates to a use of at least one glycosylated tetrafunctional amphiphilic block copolymer, as immune adjuvant.

Figure 1A:
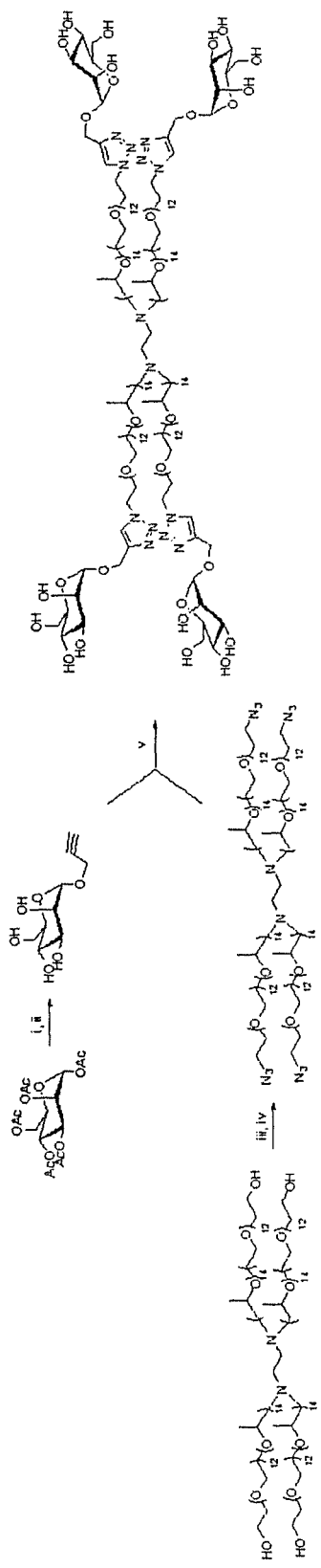

29 Claims, 6 Drawing Sheets i) Propargyl alcohol, BF$_3$ Et$_2$O, CH$_2$Cl$_2$, 2°C, 4 d ; ii) NaOCH$_3$, methanol, RT, 24 h ; iii) p-Toluenesulfonyl chloride, KOH, CH$_2$Cl$_2$, 4 Å molecular sieve, 0°C to RT, 6 d ; iv) NaN$_3$, ethanol, 80°C, 6 d ; v) CuSO$_4$·5H$_2$O, sodium ascorbate, H$_2$O, t-BuOH, 50°C, 48 h

USE OF A GLYCOSYLATED-MODIFIED TETRAFUNCTIONAL NON-IONIC AMPHIPHILIC BLOCK COPOLYMER AS IMMUNE ADJUVANT

The instant invention relates to the field of vaccination, and more particularly to novel immune adjuvants. In particular, the invention relates to the use of a glycosylated tetrafunctional non-ionic amphiphilic block copolymer as immune adjuvant.

The first adjuvant to be developed was based on water-in-oil emulsion as described by Le Moignic in 1916. Since, numerous potent adjuvants have been developed but adverse reactions due to toxic side effects have limited their use for human vaccine. In 1937, Freund have developed the Freund's adjuvant that contains a mineral oil mixed with the inactive bacteria *Mycobacterium tuberculosis*. While this adjuvant is forbidden for human use due to severe adverse effects, it remains used for veterinary vaccine (Broderson, Lab Anim Sci, 1989, 39, 400-5). In another way, Glenny et al. were the first to use aluminum salts (alum) that is the only adjuvant authorized by the Food and Drugs Administration (Gupta, R. K., Adv Drug Deliv Rev, 1998, 32, 155-172). Alum induced humoral immune response associated with a weak cellular immunity, but no mucosal immunity and may be responsible for allergic reactions. More recently squalene oil-in water emulsion (MF59) was developed and approved in Europe for influenza vaccines (Ott, G., G. L. Barchfeld, and G. Van Nest, Vaccine, 1995, 13, 1557-62; Cataldo, D. M. and G. Van Nest, Vaccine, 1997, 15, 1710-5). While theses adjuvants are able to induce a strong humoral immune response, only a weak cellular response was observed, and high toxicity is generally observed.

Different types of adjuvant have been developed based on their mechanism of action, such as liposomes-based adjuvants or immunostimulating complexes (ISCOMs). However, they are associated with hemolytic activity and local inflammatory response, and are only used in veterinary vaccines. Alternatively, immunostimulatory components, usually derived from pathogens such as lipopolysaccharide, monophosphoryl A or CpG DNA, were proposed as adjuvants, in particular for subunit vaccines, in combination with others adjuvant such as alum to elicit a strong humoral response. However, they similarly tend to induce the production of proinflamamtory cytokines, precluding their use in human (Gustafson, G. L. and M. J. Rhodes, Res Immunol, 1992, 143, 483-8). Also, while these adjuvants provide a strong humoral immune response, a weak cellular response and a lack of safety was generally observed.

Subunit vaccines are designed to include only the antigen necessary to stimulate the immune system. Subunit vaccines are well-defined, purified and may be produced in large amount with a good safety profile. However, they generally present reduced immunogenicity compared to traditional vaccines, and therefore require the use of adjuvant molecules that stimulate the immune system.

Consequently, there is a need for novel immune adjuvants able to elicit a strong immune cellular response.

There is also a need for novel immune adjuvants able to improve efficiency of subunit vaccines.

There is also a need for novel immune adjuvants able to elicit a combined strong immune cellular and humoral response.

There is also a need for novel immune adjuvants with a good safety profile suitable for human use.

There is also a need for novel immune adjuvants which may be easily produced.

There is also a need for novel immune adjuvants which may be produced at low cost.

The instant invention has for object to meet those needs.

The instant invention relates to a use of at least one glycosylated tetrafunctional non-ionic amphiphilic block copolymer, as immune adjuvant.

Unexpectedly, the inventors have observed, as detailed in the examples below, that the mannosylation of the 704 and 904 tetrafunctional non-ionic amphiphilic block copolymers allows improving dramatically not only the antibody titer (Th-2 response) but also the class I-restricted cellular response (Th-1 response) against different recombinant antigens. 704 and 904 present unique efficient and industrial characteristics including excellent safety profile.

The terms "immune adjuvant" is intended to mean, within the invention, an agent suitable for stimulating the immune system and increasing a response to a vaccine without having any specific antigenic effect in itself. An immune adjuvant of the invention is able to induce a strong immune cellular response.

According to one embodiment, an immune adjuvant according to the invention is able to induce a class I-restricted cellular immune response (or Th-1 response).

Within the invention, the terms "class I-restricted cellular immune response" is intended to mean an immune response which is mainly mediated by $CD8^1$ cytotoxic T cells. Cytotoxic T cell (also known as $T_C$, Cytotoxic T Lymphocyte, CTL, T-Killer cell, cytolytic T cell, CD8+ T-cells or killer T cell) are a sub-group of T lymphocytes capable of inducing the death of infected somatic or tumor cells. Cytotoxic T cells express T-cell receptors (TCRs) that can recognize a specific antigenic peptide bound to Class I MHC molecules and a glycoprotein called CD8, which is attracted to non-variable portions of the Class I MHC molecule. Otherwise stated, an immune adjuvant of the invention is able to induce a major histocompatibility complex (MHC) class I-restricted immune or Th-1 response.

A "protecting" class I-restricted cellular immune response is an immune response mediated by $CD8^-$ cytotoxic T cells, the intensity or level of which is able to prevent or reduce the likelihood of occurrence or treat, or alleviate or reduce symptoms of a disease triggered by a pathogen such as pathogenic bacteria, viruses, fungi, or by cancerous cells.

An immune adjuvant of the invention is not limited to stimulate a class I-restricted cellular immune response, but is also able to induce concomitantly a strong humoral response or major histocompatibility complex (MHC) class II-restricted immune (or Th-2 response). A Th2 response is an immune response characterized by the activation of B-cells to make neutralizing antibodies, leading to "humoral immunity".

According to one embodiment, an immune adjuvant according to the invention is able to induce a humoral immune response.

According to another embodiment, an immune adjuvant according to the invention is able to stimulate a mucosal immunity.

Within the invention, the terms "mucosal immunity" intends to refer to a part of the immune system which provides protection to an organism's various mucous membranes.

According to another of its objects, the instant invention relates to a use of an immune adjuvant according to the invention in a sub-unit vaccine composition.

According to another of its objects, the instant invention relates to an immune adjuvant for conferring a protecting class I-restricted cellular immune response against an antigen comprising at least one glycosylated tetrafunctional non-ionic amphiphilic block copolymer.

According to another of its objects, the instant invention relates to a vaccine composition comprising at least one antigen and, as immune adjuvant, at least one glycosylated tetrafunctional non-ionic amphiphilic block copolymer.

According to one advantage, the invention provides a novel immune adjuvant able to induce a strong and protecting class-I restricted cellular immune response.

According to another advantage, the invention provides a novel immune adjuvant with a good safety profile suitable for human use.

According to another advantage, the invention provides a novel immune adjuvant simple to produce, and obtainable at low cost.

Tetrafunctional Non-Ionic Amphiphilic Block Copolymer

Within the invention, the feature "block copolymer" intends to refer to a polymer comprising at least two sets, or blocks, of polymerized monomeric units. A "block" refers to a motif, obtained by polymerization of a monomer, and which may be repeated within the polymer. A block copolymer comprises necessarily at least two distinct kind of blocks of polymerized monomers.

Within the invention, the feature "non-ionic amphiphilic block copolymer" intends to refer to a block copolymer comprising at least one hydrophilic block and at least one hydrophobic block, the blocks being non-ionic, namely they do not contain moiety forming ion.

Within the invention, the feature "tetrafunctional" in relation with "block copolymer" refers to a compound comprising four block copolymers bound to four reactive functions born by a tetrafunctional linking moiety. Otherwise said, a "tetrafunctional block copolymer" comprises four branches of block copolymers bound to a central tetrafunctional linking moiety.

The four block copolymers may be, independently of each other, identical or different, and preferably are identical.

A tetrafunctional non-ionic amphiphilic block copolymer of the invention comprises four branches of block copolymer comprising, each, at least one hydrophilic block and at least one hydrophobic block.

A tetrafunctional non-ionic amphiphilic block copolymer of the invention is not a monophosphoryl lipid A, or an analog thereof as described in Jiang et al., Carbohydrate Res, 2007, 342:784.

A tetrafunctional non-ionic amphiphilic block copolymer of the invention is not a triterpene-saponine lipophile conjugates as described in U.S. Pat. No. 5,977,081.

In a tetrafunctional non-ionic amphiphilic block co-polymer useful for the invention the hydrophilic block may be selected in the group consisting of polyoxyalkylenes, polyvinyl alcohols, polyvinyl-pyrrolidones, poly(2-methyl-2-oxazoline), or saccharides, and the hydrophobic block may be selected in the group consisting of polyoxyalkylenes, aliphatic chains, alkylidene polyesters, polyethylene glycol with a benzyl polyether head, and cholesterol.

In particular, the hydrophilic block may be selected in the group consisting of polyoxyalkylenes, polyvinyl alcohols, polyvinyl-pyrrolidones, poly(2-methyl-2-oxazoline), and the hydrophobic block may be selected in the group consisting of polyoxyalkylenes, aliphatic chains, alkylidene polyesters, polyethylene glycol with a benzyl polyether head, and cholesterol.

More particularly, the hydrophilic block may be selected in the group consisting of polyoxyethylene, polyvinyl alcohols, polyvinyl-pyrrolidones, poly(2-methyl-2-oxazoline), and the hydrophobic block may be selected in the group consisting of polyoxypropylene, aliphatic chains, alkylidene polyesters, polyethylene glycol with a benzyl polyether head, and cholesterol.

According to one embodiment, the hydrophilic blocks of a block copolymer of the invention are comprised of, and preferably consist in, polyethylene oxide units.

According to one embodiment, the hydrophobic blocks of a block copolymer of the invention are comprised of, and preferably consist, in polypropylene oxide units.

According to a preferred embodiment, a block copolymer of the invention comprises hydrophilic blocks comprising, and preferably consisting in, polyethylene oxide units, and hydrophobic blocks comprising, and preferably consisting in, polypropylene oxide units.

In a preferred embodiment, a tetrafunctional non-ionic amphiphilic block copolymer of the invention comprises at least one terminal hydrophilic block. A "terminal hydrophilic block" is a block located at one end of a copolymer, and in particular at a distal end of a branch of a tetrafunctional polymer of the invention. Preferably, a tetrafunctional non-ionic amphiphilic block copolymer comprises at least two, preferably three, and more preferably four terminal hydrophilic blocks.

According to a preferred embodiment, a block copolymer of the invention comprises at least one, preferably two, even preferably three, and more preferably four terminal oxyethylene unit(s), each at one end of each branch of the polymer.

Preferably, a tetrafunctional non-ionic amphiphilic block copolymer of the invention comprises hydrophilic and hydrophobic blocks in a ratio hydrophilic block/hydrophobic block ranging from 0.7 to 1.5, preferably from 0.8 to 1.3, and more preferably from 0.8 to 1.2.

A tetrafunctional non-ionic amphiphilic tetrafunctional block copolymer useful for the invention may be a $(A-B)_r$—C branched block copolymers, with A representing an hydrophilic block, B representing an hydrophobic block, C representing a linking moiety, and n being 4 and figuring the number of (A-B) group linked to C.

Preferably, the hydrophilic block A is a polyoxyethylene block, the hydrophobic block B is a polyoxypropylene block.

The linking moiety C may be an alkylene diamine moiety, and preferably is an ethylene diamine moiety.

A tetrafunctional non-ionic amphiphilic block copolymer useful for the invention may be of formula (I):

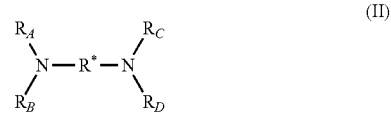

(II)

wherein $R_A$, $R_B$, $R_C$, $R_D$ represent independently of one another

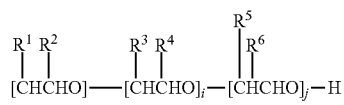

in which i has values from about 5 to about 125, in particular from about 10 to about 100, and more particularly from about 10 to about 60, and j has values from 5 to about 85, in particular from about 10 to about 50, in particular from about 10 to about 20, and more particularly equal to or greater than 13, R* is an alkylene of 2 to 6 carbons, a cycloalkylene of 5 to 8 carbons or a phenylene, and preferably is an ethylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, and if both of $R^3$ and $R^4$ are hydrogen, then one $R^5$ and $R^6$ is hydrogen and the other is methyl, or if one of $R^3$ and $R^4$ is methyl, then both of $R^5$ and $R^6$ are hydrogen.

More preferably, a non-ionic amphiphilic tetrafunctional block copolymer useful for the invention may be of formula (II):

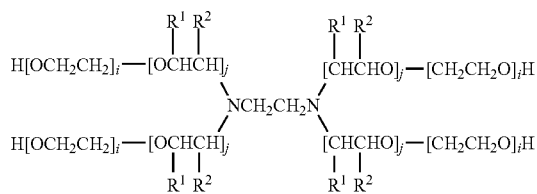

in which i has values from about 5 to about 125, in particular from about 10 to about 100, and more particularly from about 10 to about 60, and j has values from about 5 to about 85, in particular from about 10 to about 50, in particular from about 10 to about 20, and more particularly equal to or greater than 13, and wherein for each R', $R^2$ pair, one shall be hydrogen and the other shall be a methyl group.

Preferably, i may range from about 5 to about 125, in particular from about 10 to about 100, and more particularly from about 10 to about 60, and j may range from about 5 to about 50, in particular from about 10 to about 25, in particular from about 10 to about 20, and more particularly equal to or greater than 13.

A block copolymer of the invention may have a molecular weight ranging from 4000 to 35000 and in particular ranging from 4500 to 30000 and more particularly ranging from 5000 to 25000.

A block copolymer of the invention may comprise, and preferably consist in, an ethylene-oxide units content from about 40%, in particular from about 45%, in particular ranging from 45 to about 80%, in particular ranging from about 45 to 70%, and more particularly from about 45 to about 60%, and more preferably of about 50%.

A number of tetrafunctional non-ionic amphiphilic block copolymers of the invention, in particular of non-ionic amphiphilic tetrafunctional block copolymers, are commercially available under generic trade names as "poloxamines".

In particular, non-ionic amphiphilic tetrafunctional block copolymers of the invention are available from BASF (Wyandotte, Mich.) under the tradename Tetronic®.

Further details of suitable poloxamines for the invention can be found in Surfactant Systems, Eds. Attwood and Florence, Chapman and Hall, London 1983, p 356-361; in The Condensed Encyclopaedia of Surfactants, Ed. Ash and Ash, Edward Arnold, London, 1989, in Non-ionic Surfactants, pp. 300-371, Ed. Nace, Dekker, New York, 1996, in Santon, Am. Perfumer Cosmet. 72(4):54-58 (1958); (Dekker, N.Y., 1967), or in U.S. Pat. No. 6,353,055.

According to one embodiment, a non-ionic amphiphilic block copolymer suitable for the invention may be selected from a group consisting of tetrafunctional non-ionic amphiphilic block copolymer 304, tetrafunctional non-ionic amphiphilic block copolymer 704, tetrafunctional non-ionic amphiphilic block copolymer 904, tetrafunctional non-ionic amphiphilic block copolymer 908, and tetrafunctional non-ionic amphiphilic block copolymer 1107, and mixture thereof.

Preferably, a non-ionic block copolymer of the invention may be selected from a group consisting of 304, 704, 904, 1107, and mixture thereof, more preferably from a group consisting of 304, 704, 904, and mixture thereof, and more preferably from a group consisting of 704, 904, and mixture thereof.

At least one block of a block copolymer of the invention, and preferably a hydrophilic block, is conjugated with a glycosyl moiety.

A glycosylated tetrafunctional non-ionic amphiphilic block copolymer of the invention comprises at least one terminal block, and preferably one terminal hydrophilic block, conjugated with at least one glycosyl moiety.

More preferably, at least 25%, in particular at least 50%, in particular at least 75% and more particularly at least 100% of terminal blocks of a block copolymer of the invention are conjugated with a glycosyl moiety.

The amount of glycosylated tetrafunctional non-ionic amphiphilic block copolymer that may be used as immune adjuvant of the invention is to be adapted according to various parameters, such as, the amount and nature of antigen, the species, gender, weight, age, diet, conditions, additional treatment of an individual to be vaccinated. The parameters to be taken into account are well-known to a skilled man, and the adaptation of the appropriate amount of immune adjuvant to them belongs to his routine work.

A glycosylated tetrafunctional non-ionic amphiphilic block copolymer may be used in an amount ranging from 0.01 to 10% by weight of the total weight of a composition containing it, in particular ranging from 0.02 to 5%, more particularly from 0.05 to 2%, more preferably from 0.1 to 1%, more preferably from 0.1 to 0.5%, and more preferably of about 0.25%, by weight of the total weight of a composition containing it.

Glycosyl Moiety and Grafting Methods

A glycosyl moiety useful for the invention may comprise at least one glycosyl unit. A glycosyl moiety may be a single glycosyl unit or may be linear or branched polymer of glycosyl units. A glycosyl moiety may comprise from 1 to 5 glycosyl unit(s), which include 1, 2, 3, 4 and 5 glycosyl unit(s). A glycosyl moiety may preferably comprise one or two glycosyl unit(s), and preferably may contain one glycosyl unit.

A glycosyl moiety useful for the invention may be selected from mannose or galactose moieties, and preferably is a mannose moiety. A mannose moiety may comprise from 1 to 5 mannose unit(s), which includes 1, 2, 3, 4 and 5 mannose unit(s), and preferably may comprise one or two mannose unit(s), and preferably may contain one mannose unit.

A glycosyl moiety may be conjugated to a block copolymer of the invention by means of a covalent bonding established between one functional group of the glycosyl moiety and one functional group of the block copolymer. The covalent bonding may result from a reaction between the two functional groups as such or modified to be reactive. A glycosyl moiety may be directly conjugated to a block copolymer. Alternatively, a glycosyl moiety may be conjugated to a block copolymer by means of a spacer.

According to one embodiment, a glycosyl moiety may be conjugated to a block copolymer by means of an ether function.

According to another embodiment, a glycosyl moiety may be conjugated to a block copolymer of the invention by means of a spacer linking covalently one functional group of the glycosyl moiety and one functional group of the block copolymer.

A spacer is a hydrocarbon-based group, optionally comprising heteroatoms, preferably selected from N or O, and linking at least two molecules, such as a glycosyl moiety and a block copolymer, together.

A spacer useful for the invention may link one block copolymer with at least one, or with two, three, four or five, and preferably with three glycosyl moiety(ies).

When a plurality of glycosyl moiety(ies) is bound to a spacer, the glycosyl moiety(ies) may be identical or distinct from each other, and preferably they may be identical.

A spacer may be covalently linked to a block copolymer by means of an amino function.

A spacer may be covalently linked to a glycosyl moiety by means of an ether function.

A spacer may be linear or branched.

A spacer linking one block copolymer with a single glycosyl unit is a linear spacer.

A linear spacer may be covalently linked to a block copolymer by means of an amino function and may be covalently linked to a glycosyl moiety by means of an ether function.

A linear spacer may be a (hydroxymethyl)-4 triazole.

A spacer linking one block copolymer with at least two, three, four or five glycosyl moiety(ies) is a branched spacer.

The branches may be borne by a single atom or may be distributed along the main backbone of the spacer. Needless to say that, the number of branches on a single atom will depend on the valency of this atom. For example, a nitrogen atom within the main backbone of the spacer will be able to bear one branch, whereas a carbon atom will be able to bear one or two branches. Alternatively, a nitrogen atom at one end of main backbone of the spacer will be able to bear one or two branche(s), whereas a carbon atom at one end of main backbone of the spacer will be able to bear one, two or three branche(s).

Preferably, a branched spacer may comprise at least one carbon atom at one end of the main backbone bearing at least two, preferably three branches.

A spacer useful for the invention may be covalently linked to one functional group of the block copolymer, and may comprise at least one, preferably two, three, four or five, and more preferably three branches, each being covalently linked to one functional group of a glycosyl moiety.

A branched spacer may be covalently linked to a block copolymer by means of an amino function and may be covalently linked to a glycosyl moiety by means of an ether function.

A glycosyl moiety may be conjugated to a non-ionic amphiphilic block copolymer of the invention according to any known technique in the art which is to be adapted according to the nature and according to the chemical properties of both the glycosyl moiety and the copolymer block.

A glycosyl moiety may be conjugated to a hydrophilic block, in particular a terminal hydrophilic block, by chemical reaction.

A chemical reaction suitable for the invention may be performed by direct coupling or click-chemistry, in particular as detailed in the examples hereafter.

As example of block copolymers suitable for direct coupling or click-chemistry, one may mention block copolymer bearing at least one hydroxyl group, in particular from one terminal ethylene oxide unit.

As example of conjugation of at least one glycosyl moiety to a block copolymer bearing at least one hydroxyl group by direct coupling, one may mention the direct coupling between said hydroxyl group and the glycosyl moiety, for example a mannose, through a O link by reaction of a tetra-O-Acetyl-glycoside moiety with the polymer in the presence of boron trifluoride ethyl etherate, and the deprotection of the sugar by sodium methanoate.

The tetra-O-acetyl-glycoside may be obtained according to any methods known in the art. For example, one may react hydrazine acetate with penta-O-acetyl-glycoside in anhydrous solvent, such as THF. The tetra-O-acetyl-glycoside may thereafter be turned into reactive tetra-O-acetyl-1-O-trichloroacetimidoyl-glycoside in presence of potassium carbonate and trichloroacetonitrile, and in presence of an anhydrous solvent, such as dichloromethane. This compound may then be reacted with a block copolymer bearing at least one hydroxyl group, for example in presence of boron trifluoride ethyl etherate in an anhydrous solvent, such as dichloromethane to give 2,3,4,6-tetra-O-acetyl-1-O-block copolymer-glycoside. The product may be added to a solution of sodium methanoate to lead to block copolymer-glycoside.

In a preferred embodiment, the conjugation of a glycosyl moiety to a block copolymer of the invention may be performed by click-chemistry.

A click-chemistry reaction is a reaction between two functional moieties leading to the formation of at least one covalent binding between a carbon atom and a heteroatom.

Click-chemistry reactions that may be used in the invention are for example defined by Sharpless et al. (Angew Chem Int, 2001, 40, 2004-2021).

According to a preferred embodiment, functional moieties pair that may be used for the invention may be the nitrile or alcyne/azoture pair.

A click-chemistry reaction may be performed in presence of a catalyst. As useful catalyst, one may mention transition metal such as Cu.

As example of preferred chemical reaction useful for click-chemistry in accordance with the invention, one may mention the chemical reaction between an azide-functionalized compound and an alcyne-functionalized compound, in the presence of copper (Cu).

For instance, the block copolymer of the invention may be functionalized with an azide moiety, in particular on a terminal hydroxyl group, for example from an ethylene-oxide unit, whereas the glycosyl moiety to be conjugated to this modified block copolymer may be functionalized with an alcyne moiety.

As example of conjugation of at least one glycosyl moiety to a block copolymer bearing at least one hydroxyl group by click-chemistry one may mention the copper-catalysed Huisgen 1,3-dipolar cycloaddition between an azido-terminated polymer and a mannose moiety modified to contain an alkyne group.

An O-alkynyl carbohydrate, such as propargyl-β-D-glycoside, may be prepared by a reaction between β-D-carbohydrate pentaacetate, such as β-D-mannose pentaacetate, and alkynyl alcohol, such as propargyl alcohol, in dry dichloromethane in the presence of boron trifluoride ethyl etherate, followed by sodium methoxide-mediated removal of acetyl protecting groups.

A block copolymer bearing at least one hydroxyl group, for example as a terminal ethylene oxide unit, may be modified by introduction of at least one azide group according to a procedure derived from Mereyala et al., Carbohydrate Research, 1998, 307, 351; Muthana et al., J Am Chem Soc, 2007, 129, 11918; Bonger et al., Bioorg Med Chem, 2007, 15, 4841; Gonçalves et al., Pharm Res, 2005, 22, 1411-1421; Li et al., Biomacromol, 2003, 4, 1055; Iyer et al., Tetrahedron Lett, 2004, 45, 4285. The terminal hydroxyl group may be firstly converted into a bis-tosylated derivative block copolymer-OTs using an excess of p-toluenesulfonyl chloride and potassium hydroxyde in anhydrous dichloromethane. Then the sulfonate esters may be removed from the derivative block copolymer-OTs with azide ion in absolute ethanol to yield a bis-azido block copolymer.

A 1,3-dipolar cycloaddition of azide block copolymer and propargyl glycoside may be carried out using copper sulfate/sodium ascorbate in t-BuOH/$H_2O$ to yield a block copolymer-triazolo-mannose.

Antigen

According to one embodiment, an antigen to be combined with an immune adjuvant of the invention may be an antigen from bacteria, viruses, fungi, or cancerous cells.

The term "antigen" is meant a biological material (natural, recombinant or synthetic), of peptide or nucleotide-type, that stimulates a protective immune response in animals. An antigen suitable for the invention may be an amino acids sequence such as a peptide or a protein, or a nucleic acids sequence such as genomic DNA, cDNA, mRNA, tRNA, rRNA, small interference RNA (iRNA) hybrid sequences, or synthetic or semi-synthetic sequences of oligonucleotides which may or may not have been modified.

An antigen suitable for the invention may be obtained from an organism selected from the group consisting of bacteria, virus, parasite, rickettsia, protozoa and cancerous cells.

Examples of the bacteria can be selected from the group consisting of *Bordetella* spp., *Streptococcus* spp., *Staphylococcus* spp., *Clostridium* spp., *Leptospira* spp., *Escherichia* spp., *Salmonella* spp., *Pasteurella* spp., *Mycobacteria* spp., *Mycoplasma* spp., *Moraxella* spp., *Haemophilus* spp., *Borrelia* spp., *Fusobacteria* spp., *Bacteriodes* spp. and *Rhodococcus* spp.

Examples of the viruses can be selected from the group consisting of herpes viruses, parainfluenza viruses, reoviruses, rotaviruses, morbilliviruses, retroviruses, coronaviruses, adenoviruses, togaviruses, parvoviruses, parapox viruses, paramyxoviruses, cytomegaloviruses, arboviruses and hantaviruses.

Examples of parasites and protozoa can be selected from the group consisting of *Neospora* spp., *Toxoplasma* spp., *Dirofilaria* spp., *Cryptosporidium* spp., *Giardia* spp., *Babesia* spp. and *Coccidia* spp.

An example of rickettsia can be selected from the group consisting of *Chlamydia* spp., Potomac Horse Fever, *Ehrlichia canis*, and other *Ehrlichia* spp.

Examples of antigens obtained from cancerous cells can be selected from the group consisting of alphafetoprotein, Melal, NY-ESO-1, antigens BAGE, antigens MAGE, antigens GAGE, MART1, MUC1, and CA-125.

The antigens may be obtained from a whole culture of an organism such as a whole culture harvest, a partially purified whole culture harvest, a purified subunit extracted from harvest, a subunit obtained via recombinant technology and expressed in the homologous or a heterologous organism, a deletion mutant of the whole organism (conventional or rDNA gene-deleted mutants), peptides, naked DNA, chemically synthesized antigens, reverse transcribed naked cDNA or combinations thereof.

Generally, an antigen may be produced by art-known techniques of culturing and harvesting organisms, concentrating and/or conventionally purifying antigens of such organisms. For example, an antigen can be produced by: growing the selected organism in a culture having growth medium. More specifically, the organism can be grown in a tissue culture prepared from mammalian or plant cells. The organism can also be grown in fermentation media wherein the organism grows without tissue culture but has added thereto a growth medium.

The vaccines of the invention may be used in the treatment or prophylaxis of a wide range of diseases and disorders, such as:

diseases and disorders in which viruses are implicated: Retroviridae (e.g. the human immunodeficiency viruses, including HIV-1); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, Rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arenaviridae (hemorrhagic fever viruses); Reoviridae (e.g. reoviruses, orbiviurses and rotaviruses); Birnaviridae; Hepadnaviridae (Hepatitis B virus); Pariloviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the HCV virus (causing non-A, non-B hepatitis); Norwalk and related viruses, and astroviruses). Of the foregeoing, particularly preferred are HIV, Hepatitis A, Hepatitis B, Hepatitis C, rabies virus, poliovirus, influenza virus, meningitis virus, measles virus, mumps virus, rubella, pertussis, encephalitis virus, papilloma virus, yellow fever virus, respiratory syncytial virus, parvovirus, chikungunya virus, haemorrhagic fever viruses and Herpes viruses, particularly, varicella, cytomegalovirus and Epstein-Barr virus. In such embodiments the antigen(s) selected for use in a vaccine are derived from (or designed by reference to) those antigens present in the naturally-occurring virus (or expressed/induced thereby during infection).

diseases and disorders in which Gram-negative and Gram-positive bacteria are implicated: *Helicobacter pylori*, *Borelia burgdorferi*, *Legionella pneumophilia*, *Mycobacterium* spp (e.g. *M. tuberculosis*, *M. leprae*, *M avium*, *M. intracellular*, *M. kansaii* and *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus viridans*, *Streptococcus faecalis*, *Streptococcus bovis*, any of the anaerobic species of the genus *Streptococcus*, *Streptococcus pneumoniae*, *Campylobacter* spp., *Enterococcus* spp., *Haemophilus influenzae*, *Bacillus* anthracis, *Corynebacterium* spp. (including *C. diphtheriae*), *Erysipelothrix rhusiopathiae, Clostridium perfringens, Clostridium tetani, Enterobacter aerogenes, Klebsiella* spp (including *K. pneumoniae*), *Pasturella multocida, Bacteroides* spp., *Fusobacterium nucleatum, Streptobacillus monilijormis, Treponema pallidium, Treponema pertenue, Leptospira* spp., *Rickettsia* spp. and *Actinomyces* spp. (including *A. israelii*). In such embodiments the antigen(s) selected for use in the vaccine re derived from (or designed by reference to) those antigens present in the naturally-occurring bacterium (or expressed/induced thereby during infection).

diseases and disorders in which fungi are implicated: *Cryptococcus neoformans, Histoplasma capsulatum, Coccidioides immitis, Blastomyces dermatitidis, Chlamydia trachomatis* and *Candida albicans*, in such embodiments the antigen(s) selected for use in the vaccine are derived from (or designed by reference to) those antigens present in the naturally-occurring fungus (or expressed/induced thereby during infection).

diseases and disorders in which protozoa are implicated: *Plasmodium* spp. (including *Plasmodium falciparum, Plasmodium malariae, Plasmodium ovale* and *Plasmodium vivax*), *Toxoplasma* spp. (including *T. gondii* and *T. cruzii*) and *Leishmania* spp.

diseases and disorders in which cancerous cells are implicated: blood and lymphatic systems cancers (including Hodgkin's Disease, leukemias, lymphomas, multiple myeloma, and Waldenstrom's disease), melanomas (including melanoma of the eye), adenomas, sarcomas, carcinomas of solid tissues, melanoma, cancers of the lung, thyroid, salivary gland, leg, tongue, lip, bile duct, pelvis, mediastinum, urethra, Kaposi's Sarcoma (e.g. when associated with AIDS); skin cancers (including malignant melanoma), cancers of the digestive tract (including head and neck cancers, oesophageal cancer, stomach cancer, cancer of the pancreas, liver cancer, colon and rectal cancer, anal cancer), cancers of the genital and urinary systems (including kidney cancer, bladder cancer, testis cancer, prostate cancer), cancers in women (including breast cancer, cervico-uterine cancer, ovarian cancer, gynecological cancers and choriocarcinoma) as well as in brain, bone carcinoid, nasopharyngeal, retroperitoneal, thyroid, soft tissue tumours and cancers of unknown primary site. In such embodiments the antigen(s) selected for use in the vaccine re the cognate neoantigen(s) or tumour-associated antigen(s) present in the malignant cells and/or tissues.

diseases and disorders in which metazoan parasites are implicated, such as helminths (e.g. *Schistosoma* spp,).

In a preferred embodiment, an antigen useful for the invention is a peptide or protein antigen.

An antigen is naturally combined with an immune adjuvant of the invention in an immunogenically effective amount. An "immunogenically effective amount" meant that the antigen contains a protective component in a concentration sufficient to protect animals from a target disease when a vaccine containing an immune adjuvant of the invention and containing the antigen is administered to an individual. As examples of immunogenically effective amounts of an antigen, on may mention amounts ranging from 0.01 a 100 µg.

Vaccine Composition

A vaccine composition suitable for the invention may be a living vaccine, a killed or inactivated vaccine, and a subunit vaccine.

Living vaccines are generally attenuated such that they are able to mount a lengthy immune response to their antigens without producing the disease with which they are normally associated.

Killed vaccines are inactivated by chemical or other means which do not inactivate the antigenic factors which they present to the host's immune system.

For some disease vectors, even killing the organism does not prevent it from causing undesired effects in the recipient. In such cases, the agent must be fragmented into subunits or subfractions which are not, by themselves, pathogenic.

Preferably, a vaccine of the invention is a subunit vaccine.

A vaccine of the invention may be administered in any manner prescribed for the particular vaccine utilized, and preferably parenterally, that is, subcutaneously, intravenously, intramuscularly, or intraperitoneally.

A vaccine of the invention may be used in either veterinary or human therapy.

A vaccine of the invention may be prepared by dissolving or suspending an immune adjuvant of the invention in the antigen diluent and then combining suitable volumes of the immune adjuvant solution and the antigen solution at the appropriate antigen dilution. The antigen diluents are those conventional in the art, such as phosphate buffered saline, minimum essential medium, peptone and the like.

Any suitable excipient in the art may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc.

Further to an immune adjuvant of the invention, a vaccine in accordance with invention may comprise a distinct immune adjuvant. Any immune adjuvant known in the art and distinct from the inmune adjuvant of the invention may be used. As examples of additional distinct immune adjuvant one may mention complete and incomplete Freund's adjuvant, aluminium salts, squalene, or Toll-like receptor agonists, such as Poly(I:C), lipopolysaccharide, or CpG oligodeoxynucleotides.

A vaccine of the invention may take any suitable form, and include for example tablets, elixirs, capsules, solutions, suspensions, powders, granules and aerosols.

For intramuscular, intraperitoneal, subcutaneous and intravenous use, the compounds of the invention will generally be provided in sterile aqueous solutions or suspensions, buffered to an appropriate pH and isotonicity.

Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The amount of glycosylated tetrafunctional non-ionic amphiphilic block copolymer in a vaccine of the invention may vary widely according to the nature of the vaccine, the particular dosage unit employed, the period of treatment, the age, weight, kind of adjunctive treatment (if any), and sex of the patient treated, the nature and extent of the disorder treated, and the nature of the antigen administered.

The present invention will be more fully described with the aid of the following examples and figures which should be considered as illustrative and non-limiting.

FIGURES

Figure 1B:
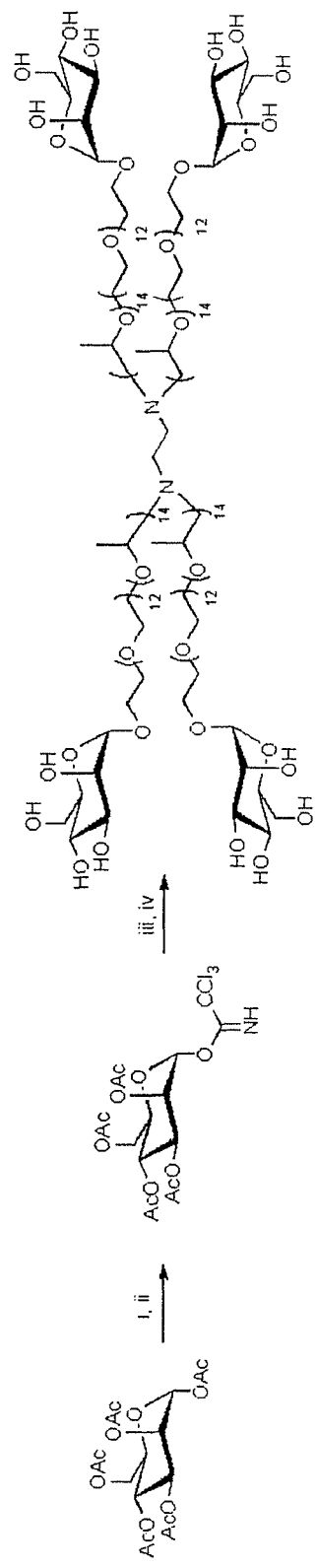

FIG. 1A and FIG. 1B illustrates the chemical synthesis pathway used to obtain mannosylated-704 by click chemistry (1A) and direct coupling (1B).

Figure 2:
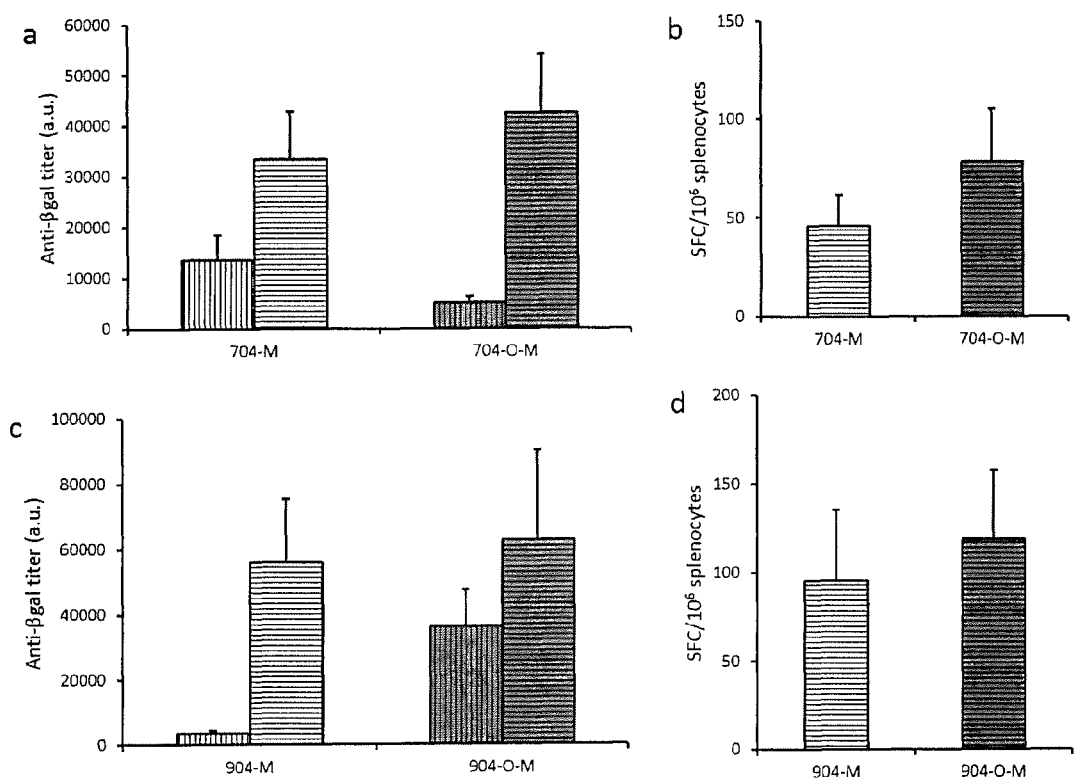

FIG. 2 illustrates the effects of way of coupling mannose to tetrafunctional polymers on the immune response after subunit vaccination. Groups of mice were injected subcutaneously on day 0 and on day 21 with β-galactosidase formulated with 0.25% 704-M, 904-M and 704-O-M, 904-O-M, synthesized by click chemistry (white bars, 704-M and 904-M) and direct coupling (grey bars, 704-O-M and 904-O-M), respectively. FIGS. 2(a) and 2(c) illustrate humoral response at day 21 (vertical hatched bars) and 42 (horizontal hatched bars) of mice injected with 25 μg β-galactosidase formulated with 704-M, 704-O-M, 904-M and 904-O-M. FIGS. 2(b) and 2(d) illustrate class I-restricted cellular response at day 42 of mice injected with β-galactosidase either formulated with 704-M, 704-O-M, 904-M and 904-O-M. For humoral response and cellular response mean titers are shown for each group+/− standard deviation for n=6 injected mice.

Figure 3:
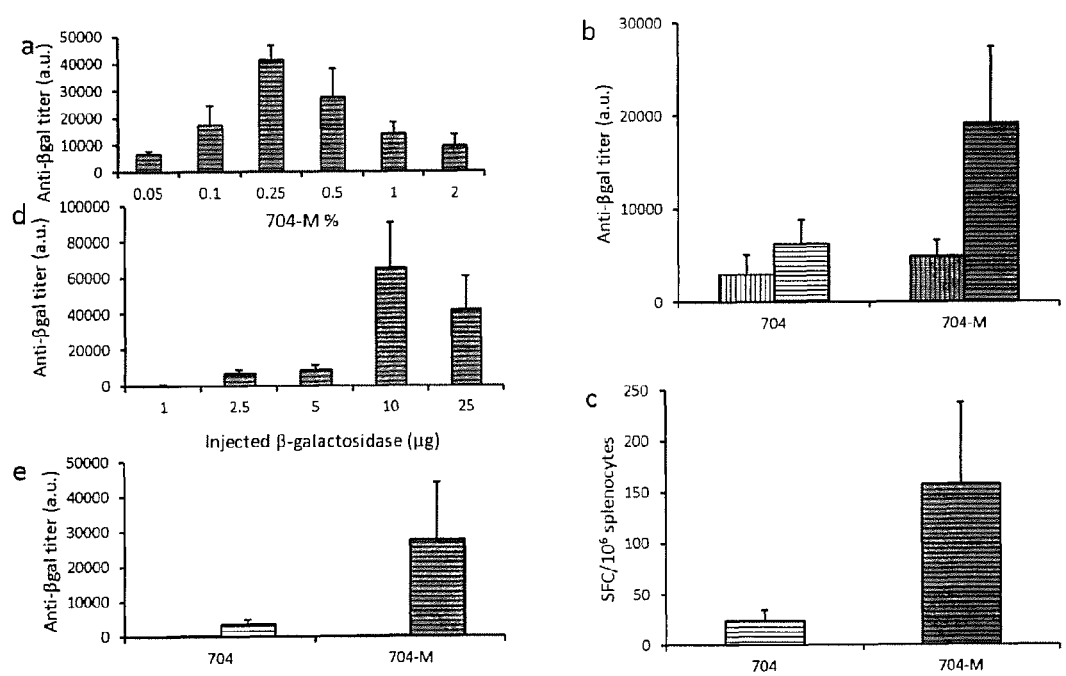

FIG. 3 illustrates the effects of 704-M targeted vectors on the immune response after subunit vaccination. Groups of mice were injected subcutaneously on day 0 and on day 21 with β-galactosidase formulated with 704 and 704-M. FIG. 3(a) illustrates the humoral response at day 42 of mice injected with 25 μg β-galactosidase formulated in complex medium with various concentrations of 704-M ranging from 0.05 to 2%. FIG. 3(b) illustrates the humoral response at day 21 (vertical hatched bars) and day 42 (horizontal hatched bars) of mice injected with β-galactosidase either formulated with 704 (white bars) or 704-M (grey bars). FIG. 3(c) illustrates a class I-restricted cellular response at day 42 of mice injected with β-galactosidase either formulated with 704 (white bar) or 704-M (grey bar). FIG. 3(d) illustrates an humoral response of mice injected with various amounts of β-galactosidase formulated with a constant 0.25% 704-M. FIG. 3(e) illustrates a humoral response at day 21 (vertical hatched bars) and day 42 (horizontal hatched bars) of Balb/c mice injected with 25 μg formulated with 0.25% 704 (white bar) or 704-M (grey bar). For humoral response and cellular response mean titers are shown for each group+/−standard deviation for n=6 injected mice.

Figure 4:
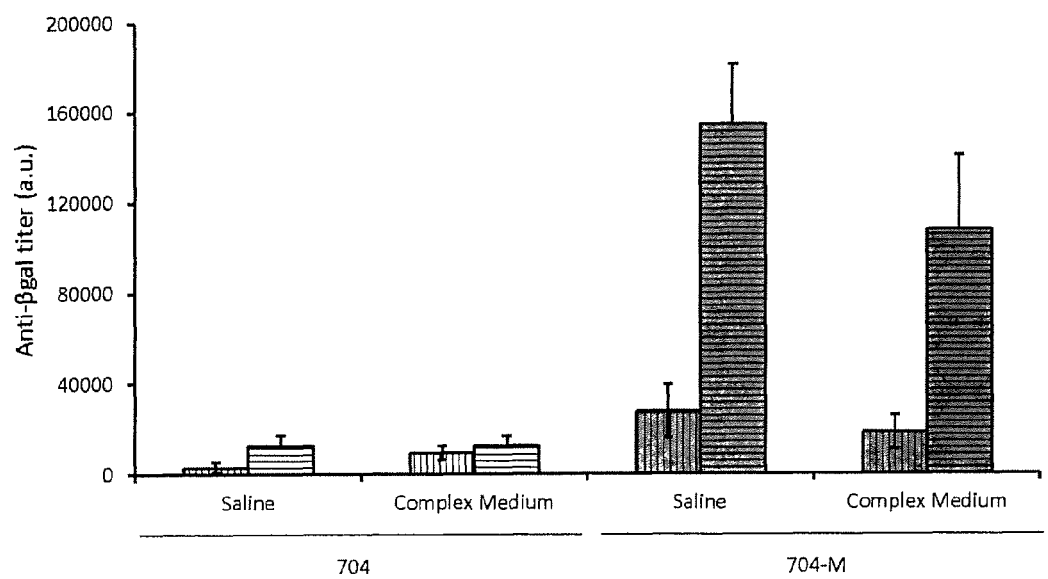

FIG. 4 illustrates the effect of formulation medium on subunit vaccination with 704 vector. Groups of mice were injected subcutaneously with 25 μg β-galactosidase formulated with 0.25% of either 704 (white bars) or 704-M (grey bars) in saline or Complex Medium. Humoral response was measured 42 days after the first injection (horizontal hatched bars) and the boost on day 21 (vertical hatched bars). For humoral response mean titers are shown for each group+/− standard deviation for n=6 injected mice.

Figure 5:
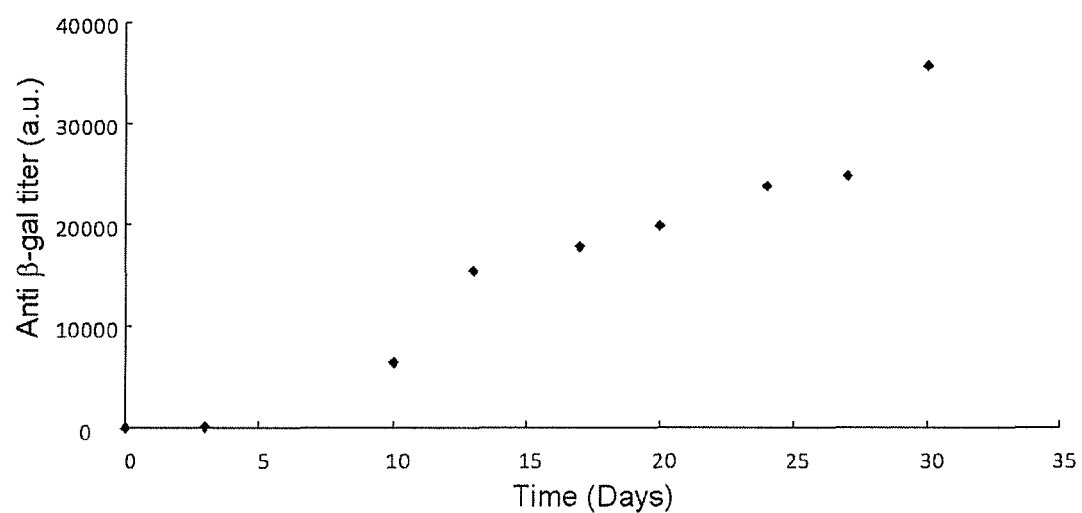

FIG. 5 illustrates the efficacy of 704-M vaccination with β-galactosidase in dog studies. Dog was s.c. injected with 150 μg β-galactosidase formulated with 704-M. β-galactosidase specific antibodies ware measured at various time points after single injection.

EXAMPLES

Material and Methods

Formulations. The 704, 904, 704-M and 904-M were kindly supplied by In-Cell-Art (Nantes, France). β-galactosidase was provided by Roche (Rosny-Sous-Bois, France). β-galactosidase or ovalbumine were formulated immediately prior sub-cutaneous (s.c.) injection. Formulation with Incomplete and Complete Freund adjuvant was performed according to the manufacturer's protocol (Sigma, St Quentin Fallavier, France).

Mannosylation of 704 and 904 by Click Chemistry (704-M and 904-M)

2-Propynyl 2,3,4,6-tetra-O-acetyl-α-D-mannopyranoside

Under nitrogen atmosphere, boron trifluoride ethyl etherate (7.90 mL, 64 mmol, 5 equiv) was added dropwise at 0° C. to a solution of α-D-mannopyranose pentaacetate (5 g, 12.8 mmol) and propargyl alcohol (2.98 mL, 51.2 mmol, 4 equiv) in anhydrous dichloromethane (150 mL) and the solution was stirred at 0° C. for 4 days. Anhydrous potassium carbonate (8 g) was added and the reaction mixture was stirred for further 1 h and filtered. The filtrate was diluted with dichloromethane (200 mL), washed with water (3×200 mL), dried over $Na_2SO_4$, filtered and concentrated to afford 2-propynyl 2,3,4,6-tetra-O-acetyl-α-D-mannopyranoside (4.95 g, quantitative yield) as a brown oil which was used without further purification. $^1H$ NMR (400 MHz, $CDCl_3$): δ=5.38-5.20 (m, 3H, $H_{2,3,4}$), 5.02 (d, J=1.6 Hz, 1H, $H_1$), 4.27 (dd, J=5.2, 12.2 Hz, 1H, $H_6$), 4.26 (d, J=2.4 Hz, 2H, $OCH_2C≡CH$), 4.10 (dd, J=2.5, 12.2 Hz, 1H, $H_6$), 4.45-3.72 (m, 1H, $H_5$), 2.46 (t, J=2.4 Hz, 1H, C≡CH), 2.15, 2.09, 2.03, 1.98 (4s, 4×3H, $OCOCH_3$); $^{13}C$ NMR (100.6 MHz, $CDCl_3$): δ=170.7, 170.0, 169.9 and 169.8 ($OCOCH_3$), 96.4 (CO, 78.0 (C≡C—H), 75.7 (C≡C—H), 69.5 ($C_5$), 69.1 ($C_4$), 69.0 ($C_3$), 66.2 ($C_2$), 62.5 ($C_6$), 55.1 ($OCH_2C≡C—H$), 20.9, 20.8×2 and 20.7 ($OCOCH_3$); MS (ESI): m/z=409.0 $[M+Na]^+$.

Propargyl-α-D-mannopyranoside

2-Propynyl 2,3,4,6-tetra-O-acetyl-α-D-mannopyranoside (990 mg, 2.56 mmol) was dissolved in a solution of sodium methoxide (69 mg, 1.28 mmol, 0.5 equiv) in dry methanol (15 mL) at room temperature. The mixture was stirred for 24 h, neutralized with DOWEX ($H^+$) resin, filtered and concentrated to afford propargyl-α-D-mannopyranoside (559 mg, quantitative yield) as an oil which was used without further purification. $^1H$ NMR (400 MHz, $D_2O$): δ=5.02 (d, J=1.6 Hz, 1H, $H_1$), 4.38-4.22 (m, 2H, $OCH_2C≡CH$), 3.98-3.56 (m, 6H, $H_{2,3,4,5,6}$), 2.90 (t, J=2.4 Hz, 1H, C≡CH); $^{13}C$ NMR (100.6 MHz, $D_2O$): δ=99.1 ($C_1$), 79.1 (C≡CH), 76.5 (C≡CH), 73.4 ($C_2$), 70.8 ($C_5$), 70.2 ($C_3$), 66.9 ($C_4$), 61.1 ($C_6$), 54.9 ($OCH_2C≡CH$); MS (ESI): m/z=240.8 $[M+Na]^-$, 218.9 $[M+H]^+$.

Tetratosylated 704 bloc copolymer: 704-OTs

Under nitrogen atmosphere, p-toluenesulfonyl chloride (416 mg, 2.18 mmol, 12 equiv) was added to a solution of 704 (1 g, 182 μmol) in anhydrous dichloromethane (16 mL) in presence of 4 Å molecular sieve. The mixture was cooled to 0° C. with an ice bath and powdered potassium hydroxide (163 mg, 2.90 mmol, 16 equiv) was carefully added in small portion at a temperature below 5° C. The mixture was stirred vigorously at room temperature for 6 days and diluted with dichloromethane (150 mL). The organic layer was washed with water (3×100 mL), dried over $Na_2SO_4$, filtered and concentrated to afford 704-OTs (948 mg, 91% of tosylated functions) as an oil which was used without further purification. $^1H$ NMR (400 MHz, $CDCl_3$): δ=7.79 (d, J=8.3 Hz, Har), 7.33 (d, J=8.3 Hz, Har), 4.15 (t, J=4.9 Hz, $CH_2OTs$), 3.70-3.30 (m, $[CH2CH_2O]_n$, $[CH_2CH(CH_3)O]_n$, $CH_2N$), 2.44 (s, $CH_3$), 1.17-1.08 (m, $[CH_2CH(CH_3)O]_n$).

Tetra-azido 704 bloc copolymer: 704-$N_3$

Sodium azide (280 mg, 4.31 mmol, 25 equiv) was added to a solution of 704-OTs (948 mg, 172 μmol) in absolute ethanol (8 mL) and the mixture was stirred vigorously at 80° C. for 6 days. The solution was then concentrated and the residue was dissolved in water (15 mL) and purified by dialysis (MCWO=2000) against MilliQ deionized water (6×1.5 L) at 4° C., followed by lyophilisation to afford 704-N$_3$ as a yellow oil (583 mg, quantitative conversion, 91% of azido functions). $^1$H NMR (400 MHz, CDCl$_3$): δ=3.70-3.30 (m, CH$_2$N$_3$, [CH$_2$CH$_2$O]$_n$, [CH$_2$CH(CH$_3$)O]$_n$, CH$_2$N), 1.17-1.07 (m, [CH$_2$CH(CH$_3$)O]$_n$); $^{13}$C NMR (100.6 MHz, CDCl$_3$): δ=75.6, 75.5, 75.3, 73.5, 73.1, 73.0, 71.0, 70.9, 70.8, 70.7 and 70.2 ([CH$_2$CH$_2$O]$_n$, [CH$_2$CH(CH$_3$)O]$_n$, CH$_2$N, CH$_2$CH$_2$N$_3$), 50.8 (CH$_2$N$_3$), 17.6 and 17.5 ([CH$_2$CH(CH$_3$)O]$_n$). Anal. Calcd for 704-N$_3$: C, 57.70; H, 9.68; N, 3.44. Found: C, 57.25; H, 9.75; N, 2.85.

Mannosylated 704: 704-Triazolo-Man (704-M)

A freshly prepared solution of copper (II) sulfate pentahydrate (90.7 mg, 364 μmol, 2 equiv) and sodium ascorbate (288 mg, 1.45 mmol, 8 equiv) in water (6 mL) was added at room temperature to a solution of propargyl-α-D-mannopyranoside (476 mg, 218 mmol, 12 equiv) in water (6 mL). The resulting mixture was added to a solution of 704-N$_3$ (1 g, 182 μmol) in tert-butanol (12 mL). After 48 h of stirring at 55° C., ethylenediaminetetraacetic acid disodium salt dihydrate (EDTA, 677 mg, 1.82 mmol, 10 equiv) in water (15 mL) was added and stirring was continued for 30 min at room temperature. The crude reaction mixture was purified by dialysis (Cellu•Sep® H1 dialysis membrane 1,000 MCWO) against MilliQ deionized water (6×1.5 L) at 4° C., followed by lyophilisation to afford 704-Triazolo-Man as a brown oil (221 mg, up to 85% of mannose incorporation). $^1$H NMR (400 MHz, D$_2$O): δ=8.11 (s, 4H, H triazol), 4.95 (s, 4H, H$_1$ mannose), 4.83 (d, J=12.4 Hz, 4H, OCH$_2$-triazol), 4.70 (d, J=12.4 Hz, 4H, OCH$_2$-triazol), 4.63 (t, J=4.8 Hz, 8H, OCH$_2$CH$_2$N), 3.97 (t, J=4.8 Hz, 8H, OCH$_2$CH$_2$N), 3.92-3.25 (m, H$_{2,3,4,5,6}$ galactose, CH$_2$N, [CH$_2$CH$_2$O]$_n$, [CH$_2$CH(CH$_3$)O]$_n$), 1.42-0.89 (m, [CH$_2$CH(CH$_3$)O]$_n$); $^{13}$C NMR (100.6 MHz, D$_2$O): δ=143.8 (NCH=C), 126.0 (NCH=C), 99.7 (C$_1$ mannose), 75.8, 75.7, 75.6, 74.8, 73.3, 72.6, 72.3, 70.8, 70.3, 69.9, 69.8, 69.1, 67.9, 67.0, 61.2, 60.0, 50.4, 17.5, 16.4.

The same procedure as above-described was applied to prepare mannosylated 904 by click-chemistry (904-M).

Mannosylation of 704 and 904 by O link (704-O-M and 904-O-M)

2,3,4,6-tetra-O-acetyl-D-mannopyranoside

Under inert atmosphere, hydrazine acetate (190 mg, 2.06 mmol, 1.35 Eq) is added to a solution of penta-O-acetyl-α-D-mannopyranoside (596 mg 1.53 mmol) in anhydrous THF (6 mL) in presence of a 4 Å molecular sieve. The mixture was stirred at room temperature for 4 h30, concentrated under reduced pressure and purified by silica gel chromatography (CH$_2$Cl$_2$/CH$_3$OH; 25:1) to yield 2,3,4,6-tetra-O-acetyl-D-mannopyranoside (383.3 mg, 78%) as a yellow oil. RMN $^1$H (CDCl$_3$): δ=5.41 (m, 0.5H, H$_{1α}$), 5.40 (m, 0.5H, H$_{1β}$), 5.31-5.19 (m, 3H, H$_{4,3,2}$), 4.30-4.06 (m, 3H, H$_{5,6a,6b}$), 2.21-1.98 (m, 12H, CH$_3$CO). RMN $^{13}$C (100.6 MHz, CDCl$_3$): δ=176.2, 171.2, 170.5 et 170.2 (C=O), 92.6 (C$_1$), 71.5 (C$_4$) 69.2 (C$_3$), 68.9 (C$_2$), 66.6 (C$_5$), 62.9 (C$_6$), 21.3, 21.2, 21.1 et 20.9 (4×CH$_3$CO).

2,3,4,6-tetra-O-acetyl-1-O-trichloroacetimidoyl-α-D-mannopyranoside

Under inert atmosphere, potassium carbonate (836 mg, 6.05 mmol, 6.7 Eq) and trichloroacetonitrile (0.78 mL, 7.8 mmol, 8.8 Eq) are successively added to solution of 2,3,4,6-tetra-O-acetyl-D-mannopyranoside (310 mg, 0,89 mmol) in anhydrous dichloromethane (20 mL) in presence of a 4 Å molecular sieve. The mixture was stirred at room temperature for 12 h then filtered et evaporated to yield 2,3,4,6-tetra-O-acetyl-1-O-trichloroacetimidoyl-α-D-mannopyranoside (457 mg, 96%) as a uncolored oil.

2,3,4,6-tetra-O-acetyl-1-O-704-α-D-mannopyranoside (704-manAc4):

Under nitrogen atmosphere, boron trifluoride ethyl etherate (200 μL, 1.62 mmol, 25 equiv) was added at room temperature to a solution of 704 (377.6 mg, 69 μmol) and 2,3,4,6-tetra-O-acetyl-α-D-mannopyranoside trichloroacetamidate (509.4 mg, 1.03 μmol, 15 equiv) in anhydrous dichloromethane (20 mL) and the reaction mixture was stirred at room temperature for 2 h. The solution was concentrated under reduced pressure, diluted with phosphate buffer (pH 7, 4 mL) and purified by dialysis (Cellu•Sep® H1 dialysis membrane 2,000 MCWO) against MilliQ deionized water (6×1.5 L) at 4° C., followed by lyophilisation to afford 704-ManAc$_4$ as a yellow oil (290 mg, up to 35% of acetylated mannose incorporation). $^1$H NMR (400 MHz, CDCl3): δ=5.36 (dd, J=3.4, 10.1 Hz, 1H, H$_4$), 5.30-5.25 (m, 2H, H$_2$, H$_3$), 4.86 (d, J=3.3 Hz, 1H, H$_1$), 4.34-4.13 (m, 4H, CH$_2$OgalAc$_4$, H$_5$, H$_6$), 3.80-3.21 (m, [CH$_2$CH$_2$O]$_n$, [CH$_2$CH(CH$_3$)O]$_n$, CH$_2$N), 2.15, 2.10, 2.03 et 1.98 (4×s, 4×3H, CH$_3$CO), 1.15-1.05 (m, [CH$_2$CH(CH$_3$)O]$_n$); RMN $^{13}$C (100.6 MHz, CDCl$_3$): δ 97.9 (C$_1$), 77.5, 77.2, 76.8, 75.7, 75.5, 73.5, 73.0, 72.7, 71.0, 70.7, 70.5, 70.1, 69.2 (C$_2$), 68.7(C$_4$), 66.3, 62.6, 61.9 (C$_6$), 29.8, 21.0×2 et 20.8 (4×CH$_3$CO), 17.6, 17.4.

1-O-704-α-D-Mannopyranoside 704 bloc copolymer: 704-O-M

The product 704-manAc4 (296 mg, 43 μmol) was added to a solution of sodium methanoate freshly prepared (200 mM, 1.7 mmol, 29 eq.), stirred at room temperature for 2 hours and then concentrated under reduce pressure, diluted with phosphate buffer (pH 7, 4 mL) and purified by dialysis (Cellu•Sep® H1 dialysis membrane 2,000 MCWO) against MilliQ deionized water (6×1.5 L) at 4° C., followed by lyophilisation to lead 704-Man as a yellow oil (246 mg, up to 35% of acetylated mannose incorporation). $^1$H NMR (400 MHz, CDCl$_3$): δ=4.87 (d, J=3.4 Hz, 1H, H$_1$), 3.85-3.75 (m, 2H, CH$_2$OGal), 3.70-3.25 (m, H$_{2,3,4,5,6}$ [CH$_2$CH$_2$O]$_n$, [CH$_2$CH(CH$_3$)O]$_n$, CH$_2$N), 1.22-1.02 (m, [CH$_2$CH(CH$_3$)O]$_n$); RMN $^{13}$C (100.6 MHz, CDCl$_3$): δ=100.5 (C$_1$), 77.7, 77.4, 77.1, 76.2, 75.9, 75.7 (C$_5$), 74.9 (C$_3$), 74.2, 74.0, 73.7, 73.3 (C$_2$), 73.0, 72.3 (C$_4$), 72.1, 71.2, 70.9 70.6, 68.9, 67.1, 62.1 (C$_6$), 18.9, 18.6, 17.8, 17.7.

The same procedure as above-described was applied to prepare mannosylated 904 by direct coupling (904-O-M).

Animal procedures. C57bl/6 female mice (Janvier, Le Genest Saint Isle, France), 8 weeks old were used for experiments. Animals were housed in plastic boxes of standard dimensions for housing mice. Animals were placed in an air-conditioned (15-21° C.) environment. The artificial day/night light cycle involved 12 hours light and 12 hours darkness with light on at 8:00 a.m. Prior to each injection, mice were anaesthetized by isofluorane. Recombinant proteins-synthetic formulations were injected using a U100 microfine syringe (BD Medical Rungis, France). Each animal was subcutaneous (s.c.) injected with 100 μl following a prime/boost scheme on day 0 and 21. Blood samples were collected on day 0, 21 and 42 for all mice from retro orbital sinus using a glass pipette. Blood samples were warmed up at 37° C. for 30 minutes and then centrifuged at 5000 rpm for 5 minutes. Serum was collected and stored at −80° C. On day 42 mice were sacrificed, blood samples were collected and spleen was used for ELISPOT analysis.

Beagle male dog (ENV, Nantes, France) was subcutaneously injected in the interscapular region with 150 μg of β-galactosidasae recombinant protein formulated with 0.25% 704-M in a Tyrode's medium (CaCl$_2$ 3 mM, MgCl$_2$ 2 mM, KCl 6 mM, NaCl 140 mM, glucose 10 mM, and Hepes 10 mM, pH 7.4; Tyrode Pharmacology. Philadelphia, 1908, 2nd Edition, 1912). Formulation of 1 ml was injected using a 2.5 ml syringe with 21G needle.

Measurement of the immune response. Mouse antibodies (total IgG) titer specific for β-galactosidase was measured by ELISA. β-galactosidase protein was used to coat the wells overnight at 4° C. After one hour saturation with BSA at ambient temperature, dilutions of serum were incubated at 37° C. during one hour and a half. Then, peroxidase-conjugated goat anti-mouse IgG, diluted at 1/5000, was incubated at ambient temperature during one hour and after addition of the peroxydase substrate, plates were read spectrophotometrically at 490 nm. For each mouse, pre immune, pre boost 1 and final serum were tested at 4 dilutions: 1/20, 1/200, 1/2000, 1/20000. Titer of the standard was arbitrary fixed at 5000, and was diluted from 1/1000 to 1/64000 to build the calibration curve. Each tested dilution samples with OD included in the linear part of the calibration curve were conserved for antibody titer determination. Other dilutions were excluded.

Dog antibodies (total IgG) titer specific for β-galactosidase was measured by ELISA as described above with some minor modifications. Briefly, peroxidase-conjugated goat anti-dog IgG was used at 1/5000 dilution. Titer of the standard was arbitrary fixed at 5000. Mouse antibodies (total IgG) titer specific for ovalbumine was measured by ELISA by adapting the protocol described for the determination of mouse anti-β-galactosidase titer.

Class I-restricted IFNγ secretion was determined by ELISPOT (Diaclone, Besancon, France), as a marker for the presence of βGal CTL. The H2-Kb restricted ICPMYARV peptide was used as a representative βGal epitope. The negative control was the KRWIILGLNK peptide (HIV gag 263-272). Live splenocytes were counted on a hemocytometer slide by Trypan blue exclusion, resuspended at $1 \times 10^6$/ml in complete medium (RPMI 1640 supplemented with 10% fetal calf serum, 2 mmol/l 1-glutamine, penicillin, and streptomycin—all from Invitrogen, Paisley, UK), then distributed in triplicate at $1 \times 10^5$ cells/well. Cells were incubated overnight at 37° C. and 5% $CO_2$ in the presence of 5 µg/ml Concanavalin A or 4 µg/ml peptide. SFCs were detected according to the manufacturer's protocol, automatically counted on an AID ELISPOT reader (Autoimmun Diagnostika, Strassberg, Germany) and results expressed as SFC/million splenocytes. To correct for cell counting errors, peptide-specific SFC counts from the n th mouse were normalized by multiplying by Mean ConA stimulated SFC over all wells divided by ConA stimulated SFC from the n th mouse. Normalization was consistently found to reduce the within-group variance. Class I-restricted IFNγ secretion was also determined by ELISPOT as described above for the quantification of ovalbumine CD8 specific cells. The H2-Kb restricted SIINFEKL peptide was used as a representative ovalbumine epitope.

Example 1

Synthesis and Characterization of Mannosylated Block Copolymers

To test the potential of targeted vectors as adjuvant for subunit vaccination, amphiphilic tetrafunctional block copolymers were chemically modified by introducing a mannose targeting ligand. Then, their ability to induce humoral and cellular responses was analyzed after formulation with recombinant antigen and subcutaneous injection.

The incorporation of mannosyl residues at the distal extremities of the tetrafunctional amphiphilic block copolymer 704 was performed following two chemical strategies (FIG. 1); (a) by click chemistry relying on the copper-catalysed Huisgen 1,3-dipolar cycloaddition between the azido-terminated polymer and the mannose moiety that contains an alkyne group (FIG. 1a), and (b) by the direct coupling between the hydroxyl group of the tetrafunctional polymers and the mannose through a O link by reaction of a 2,3,4,6-tetra-O-Acetyl-1-O-α-D mannopyranoside with the polymers in the presence of boron trifluoride ethyl etherate, and the deprotection of the sugar by sodium methanoate (FIG. 1b). Mannosylated 704 obtained by click chemistry and direct coupling were respectively named 704-M and 704-O-M. For the click chemistry approach, the required O-alkynyl carbohydrate was easily prepared by the reaction between β-D-mannose pentaacetate and propargyl alcohol in dry dichloromethane in the presence of boron trifluoride ethyl etherate, followed by sodium methoxide-mediated removal of acetyl protecting groups. Propargyl-β-D-mannopyranoside was obtained in a quantitative yield without formation of the undesired α-anomer.

The introduction of azide groups at the PEO terminus of the tetrafunctionnal 704 was developed using a modified two steps procedure that had been previously applied to polyethylene glycol (Mereyala et al., Carbohydrate Research, 1998, 307, 351; Muthana et al., J Am Chem Soc, 2007, 129, 11918; Bonger et al., Bioorg Med Chem, 2007, 15, 4841; Gonçalves et al., Pharm Res, 2005, 22, 1411-1421; Li et al., Biomacromol, 2003, 4, 1055; Iyer et al., Tetrahedron Lett, 2004, 45, 4285). The hydroxy distal extremities 704 were converted into the bis-tosylated derivative block copolymer-OTs using an excess of p-toluenesulfonyl chloride (3 equivalents per hydroxyl group) and potassium hydroxyde in anhydrous dichloromethane. The conversion of hydroxyl groups was determined by $^1H$ NMR experiments at 400 MHz using the comparative integration of the PPO $CH_3$ signal at $\delta=1.18$-1.03 ppm (multiplet, 150H) and the terminal PEO methylene $CH_2OTs$ signal at $\delta=4.14$ ppm or the tosyl aromatic signals at $\delta=7.78$ and 7.33 ppm. This method indicated that up to 91% of the terminal extremities of the 704 was functionnalized. The complete displacement of the sulfonate esters of 704-OTs with azide ion was performed in absolute ethanol at 80° C. and yielded the bis-azido 704-$N_3$. $^1H$ NMR analyses showed a total disappearance of the tosyl aromatic signals and a downshift of the terminal PEO methylene protons signal to the broad —$OCH_2CH_2$— signal. $^{13}C$ NMR experiments also confirmed the quantitative conversion of sulfonate esters in azide with a unique signal of terminal PEO methylene carbons at $\delta=50.8$ ppm corresponding to the —$CH_2N_3$ signal.

The optimized 1,3-dipolar cycloaddition of azide 704-N3 and propargyl-β-D-mannosepyranoside was carried out using copper sulfate/sodium ascorbate in t-BuOH/$H_2O$ (1:1, v/v) at 55° C. for 2 days to yield the block copolymer 704 Triazolo-Mannose containing up to 85% of mannose residues at the 704-M distal extremities. The regiospecific formation of the 1,4-triazole ring was verified by $^1H$ and $^{13}C$ NMR and the incorporation of mannose was calculated using the comparative integration of the PPO $CH_3$ signal and the triazol or the pyranoside signals. Quantification of the mannose incorporation in 704, using the second chemical synthesis by direct coupling to form the 1-O-Polymer-α-D-Mannose led to 80% of mannose residues at the 704-O-M distal extremities. The described synthesis of mannosylated 704 either by click chemistry or direct O-link was also applied to the mannosylation of tetrafunctional block copolymer 904.

Analysis by Maldi-Tof of the molecular repartition of 704 and 904 mannosylated or not did not show differences (data not shown).

Example 2

Mannosylated 704 and 904 by the Two Different Chemical Strategies Led to Immune Responses to s.c. Subunit Vaccination The influence of the way of coupling mannose to 704 and 904 tetrafunctional polymers on the vaccination efficiency was investigated. To this end, mice were injected subcutaneously on day 0 and day 21 with recombinant β-galactosidase formulated with mannosylated 704 and 904 either by click chemistry (704-M and 904-M) or direct O-link (704-O-M and 904-0-M). Results (FIG. 2) show that at day 42 both cellular and humoral responses to β-galactosidase were the same irrespective of the way of coupling mannose to the two tetrafunctional polymers tested.

Example 3

Optimization of Formulation Parameters with 704-M for High Humoral and Cellular Responses Mice were subcutaneously injected on day 0 and day 21 with recombinant β-galactosidase formulated with various amount of 704-M. Mice were killed at day 42 after the first β-galactosidase injection to compare levels of anti-β-galactosidase titer in the different groups. Significant enhancement of humoral response was observed and peaked for formulation containing 0.25% 704-M (FIG. 3a).

Next, the effect of targeted vector compared to the parent vector was investigated. To this end, mice were injected subcutaneously on day 0 and day 21 with 25 µg of β-galactosidase either formulated with 704-M and parent 704. Each vector was used at the concentration of 0.25% that gave maximal enhancement of anti β-galactosidase antibody titer. Significant enhancement of anti β-galactosidase titer at day 42 was observed with 704-M compared to the parent 704 vector (FIG. 3b). Most importantly, class I-restricted cellular immune response showed also an increase in group of mice injected with 704-M (FIG. 3c).

Dose response experiments using β-galactosidase formulated with 0.25% 704-M showed that maximal humoral response was obtained with 10 µg β-galactosidase (FIG. 3d). The influence of mouse strain on 704 and 704-M vaccination efficiency was also investigated. FIG. 3e shows that, increased in anti β-galactosidase antibody titer was also observed in Bal/c mice with 704-M compared to that obtained with 704 parent.

Example 4

Formulation Medium Does Not Affect the Vaccination Efficiency of Mannosylated 704

The efficacy of 704 and 704-M was then tested in different formulation medium. Mice were injected subcutaneously on day 0 and day 21 with β-galactosidase formulated with 704 and 704-M either in saline or in a Tyrode's medium. Results show that the medium composition used for the formulation did not modify the anti β-galactosidase antibody titer in group of mice immunized either with 704 or 704-M (FIG. 4). Results also confirm the dramatic increase of humoral response obtained at day 42 when 704 chemically modified with a mannose targeting moiety.

Example 5

704-M Elicit Recombinant Vaccination in Large Animals

To extend our finding on large animal, dogs received a single s.c. injection at day 0 with 150 µg β-galactosidase formulated with 704-M. Results show that humoral response was detectable 10 days after a single injection and continuously increased over time (FIG. 5).

BIBLIOGRAPHY

Broderson, J. R., *Lab Anim Sci*, 1989, 39, 400-5
Gupta, R. K., *Adv Drug Deliv Rev*, 1998, 32, 155-172.
Ott, G., G. L. Barchfeld, and G. Van Nest, *Vaccine*, 1995, 13, 1557-62.
Cataldo, D. M. and G. Van Nest, *Vaccine*, 1997, 15, 1710-5.
Gustafson, G. L. and M. J. Rhodes, Res Immunol, 1992, 143, 483-8; discussion 573-4.
Mereyala, H. B.; Gurrala, S. R. *Carbohydrate Research* 1998, 307, 351-354.
Muthana, S.; Yu, H.; Huang, S.; Chen, X. *Journal of the American Chemical Society* 2007, 129, 11918-11919.
Bonger, K. M.; van den Berg, R. J. B. H.; Heitman, L. H.; IJzerman, A. P.; Oosterom, J.; Timmers, C. M.; Overkleeft, H. S.; van der Marel, G. A. *Bioorganic & Medicinal Chemistry* 2007, 15, 4841-4856.
Gonçalves, M.; Estieu-Gionnet, K.; Berthelot, T.; Laïn, G.; Bayle, M.; Canron, X.; Betz, N.; Bikfalvi, A.; Déléris, G. *Pharmaceutical Research* 2005, 22, 1411-1421.
Li, J.; Kao, W. J. *Biomacromolecules* 2003, 4, 1055-1067.
Iyer, S. S.; Anderson, A. S.; Reed, S.; Swanson, B.; Schmidt, J. G. *Tetrahedron Letters* 2004, 45, 4285-4288.

The invention claimed is:

1. A method for inducing an immune response in a subject in need thereof, comprising administering to said subject at least one glycosylated tetrafunctional non-ionic amphiphilic block copolymer, as an immune adjuvant.

2. The method according to claim 1, wherein said immune adjuvant induces a class I-restricted cellular immune response.

3. The method according to claim 1, wherein said immune adjuvant induces a humoral immune response.

4. The method according to claim 1, wherein said immune adjuvant stimulates a mucosal immunity.

5. The method according to claim 1, wherein said immune adjuvant is in a sub-unit vaccine composition.

6. The method according to claim 1, wherein said at least one glycosylated tetrafunctional non-ionic amphiphilic block copolymer comprises a tetrafunctional non-ionic amphiphilic block copolymer comprising at least one terminal hydrophilic block.

7. The method according to claim 1, wherein said at least one glycosylated tetrafunctional non-ionic amphiphilic block copolymer comprises hydrophilic blocks comprising polyethylene oxide units and hydrophobic blocks comprising polypropylene oxide units.

8. The method according to claim 1, wherein said at least one glycosylated tetrafunctional non-ionic amphiphilic block copolymer comprises a tetrafunctional non-ionic amphiphilic block copolymer of formula (II):

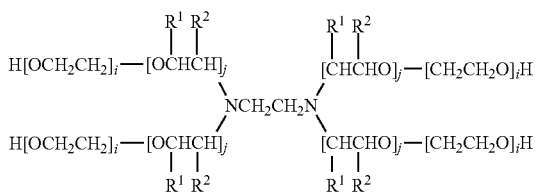

in which
i ranges from about 5 to about 125, and
j ranges from about 5 to about 85,
wherein for each $R^1$, $R^2$ pair, one is a hydrogen atom and the other is a methyl group.

9. The method according to claim 1, wherein at least one glycosyl moiety in said at least one glycosylated tetrafunctional non-ionic amphiphilic block copolymer is conjugated by means of a spacer linking covalently one functional group of the at least one glycosyl moiety and one functional group of a tetrafunctional non-ionic amphiphilic block copolymer.

10. The method according to claim 1, wherein said at least one glycosylated tetrafunctional non-ionic amphiphilic block copolymer comprises a tetrafunctional non-ionic amphiphilic block copolymer comprising at least one terminal hydrophilic block conjugated with a glycosyl moiety.

11. The method according to claim 1, wherein said at least one glycosylated tetrafunctional non-ionic amphiphilic block copolymer comprises a tetrafunctional non-ionic amphiphilic block copolymer wherein at least 25% of terminal hydrophilic blocks of said tetrafunctional non-ionic amphiphilic block copolymer are conjugated with a glycosyl moiety.

12. The method according to claim 1, wherein said at least one glycosylated tetrafunctional non-ionic amphiphilic block copolymer comprises a glycosyl moiety comprising at least one glycosyl unit.

13. The method according to claim 1, further comprising administering an antigen, wherein said antigen is a peptide or protein antigen.

14. An immune adjuvant for conferring a protecting class I-restricted cellular immune response against an antigen comprising at least one glycosylated tetrafunctional non-ionic amphiphilic block copolymer.

15. A vaccine composition comprising at least one antigen and, as immune adjuvant, at least one glycosylated tetrafunctional non-ionic amphiphilic block copolymer.

16. The immune adjuvant according to claim 14, wherein said at least one glycosylated tetrafunctional non-ionic amphiphilic block copolymer comprises a tetrafunctional non-ionic amphilic block copolymer comprising at least one terminal hydrophilic block.

17. The immune adjuvant according to claim 14, wherein said at least one glycosylated tetrafunctional non-ionic amphiphilic block copolymer comprises hydrophilic blocks comprising polyethylene oxide units and hydrophobic blocks comprising polypropylene oxide units.

18. The immune adjuvant according to claim 14, wherein said at least one glycosylated tetrafunctional non-ionic amphiphilic block copolymer comprises a tetrafunctional non-ionic amphiphilic block copolymer of formula (II):

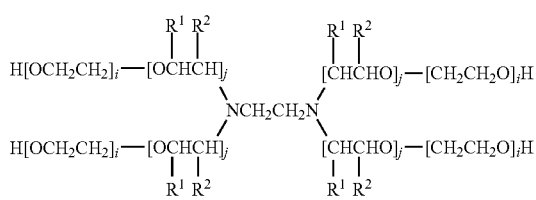

in which
i ranges from about 5 to about 125, and
j ranges from about 5 to about 85,
wherein for each $R^1$, $R^2$ pair, one is a hydrogen atom and the other is a methyl group.

19. The immune adjuvant according to claim 14, wherein at least one glycosyl moiety in said at least one glycosylated tetrafunctional non-ionic amphiphilic block copolymer is conjugated by means of a spacer linking covalently one functional group of the at least one glycosyl moiety and one functional group of a tetrafunctional non-ionic amphiphilic block copolymer.

20. The immune adjuvant according to claim 14, wherein said at least one glycosylated tetrafunctional non-ionic amphiphilic block copolymer comprises a tetrafunctional non-ionic amphiphilic block copolymer comprising at least one terminal hydrophilic block conjugated with a glycosyl moiety.

21. The immune adjuvant according to claim 14, wherein said at least one glycosylated tetrafunctional non-ionic amphiphilic block copolymer comprises a tetrafunctional non-ionic amphiphilic block copolymer wherein at least 25% of terminal hydrophilic blocks of said tetrafunctional non-ionic amphiphilic block copolymer are conjugated with a glycosyl moiety.

22. The immune adjuvant according to claim 20, wherein said glycosyl moiety comprises at least one glycosyl unit.

23. The vaccine composition according to claim 15, wherein said at least one glycosylated tetrafunctional non-ionic amphiphilic block copolymer comprises a tetrafunctional non-ionic amphiphilic block copolymer comprising at least one terminal hydrophilic block.

24. The vaccine composition according to claim 15, wherein said at least one gylcosylated tetrafunctional non-ionic amphiphilic block copolymer comprises tetrafunctional non-ionic amphiphilic block copolymer comprising hydrophilic blocks comprising polyethylene oxide units and hydrophobic blocks comprising polypropylene oxide units.

25. The vaccine composition according to claim 15, wherein said at least one glycosylated tetrafunctional non-ionic amphiphilic block copolymer comprises a tetrafunctional non-ionic amphiphilic block of formula (II):

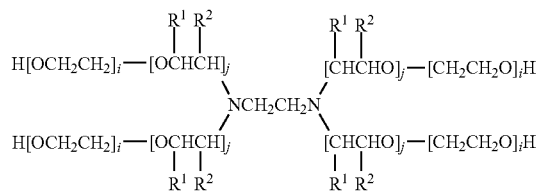

in which
i ranges from about 5 to about 125, and
j ranges from about 5 to about 85,
wherein for each $R^1$, $R^2$ pair, one is a hydrogen atom and ther other is a methyl group.

26. The vaccine composition according to claim 15, wherein at least one glycosyl moiety in said at least one glycosylated tetrafunctional non-ionic amphiphilic block copolymer is conjugated by means of a spacer linking covalently one functional group of the at least one glycosyl moiety and one functional group of a tetrafunctional non-ionic amphiphilic block copolymer.

27. The vaccine composition according to claim 15, wherein said at least one glycosylated tetrafunctional non-ionic amphiphilic block copolymer comprises a tetrafuntional non-ionic amphiphilic block copolymer comprising at least one terminal hydrophilic block conjugated with a glycosyl moiety.

28. The vaccine composition according to claim 15, wherein said at least one glycosylated tetrafunctional non-ionic amphiphilic block copolymer comprises a tetrafunctional non-ionic amphiphilic block copolymer wherein at least 25% of terminal hydrophilic blocks of said tetrafunctional non-ionic amphiphilic block copolymer are conjugated with a glycosyl moiety.

29. The vaccine composition according to claim 27, wherein said glycosyl moiety comprises at least one glycosyl unit.

\* \* \* \* \*